United States Patent [19]
Ferguson

[11] Patent Number: 5,161,196
[45] Date of Patent: Nov. 3, 1992

[54] APPARATUS AND METHOD FOR REDUCING MOTION SICKNESS

[76] Inventor: John L. Ferguson, 11805 Trailridge Dr., Potomac, Md. 20854

[21] Appl. No.: 618,263

[22] Filed: Nov. 21, 1990

[51] Int. Cl.$^5$ .............................................. H04R 3/00
[52] U.S. Cl. ........................................ 381/1; 381/17; 381/63
[58] Field of Search ................................ 381/1, 17, 63

[56] References Cited

U.S. PATENT DOCUMENTS

| | | |
|---|---|---|
| 1,907,402 | 5/1933 | Fedor . |
| 2,288,683 | 7/1942 | Clancy . |
| 2,745,091 | 5/1956 | Leffler . |
| 3,461,423 | 8/1969 | Trumble . |
| 3,548,400 | 12/1970 | Boyd et al. . |
| 4,052,720 | 10/1977 | McGregor et al. . |
| 4,283,798 | 8/1981 | Kuehn . |
| 4,284,987 | 8/1981 | Gibson et al. . |
| 4,562,589 | 12/1985 | Warnaka et al. . |
| 4,817,149 | 3/1989 | Myers .................................... 381/63 |

OTHER PUBLICATIONS

A. Rolnick, PH.D. & W. Bles Ph.D., Performance and Well-Being . . . , pp. 779-785 Aug. 1989.
Marc E. Cook, The Art of Noise, Dec. 1989, pp. 65-69.
Philip Elmer-Dewitt, Fighting Noise with Antinoise, Dec. 1989, p. 94, et seq.
Terence J. Lyons, M.D., M.P.H. et al., The Effects of Acoustic . . . , Aug. 1990, pp. 699-706.
George Gourevitch, Directional Hearing in Terrestrial Mammals, pp. 357-373.
Capt. Alvina Mitchell, Study opens ears on 3-D sound, Oct. 1990, vol. 14, No. 19, p. 1.

Primary Examiner—Jin F. Ng
Assistant Examiner—Edward Lefkowitz
Attorney, Agent, or Firm—Dowell & Dowell

[57] ABSTRACT

An artificial horizon of sound is maintained in an enclosure which is irregularly moving in a manner which may induce motion sickness of its occupant(s), by positioning sound emitters in spaced locations in the enclosure and continuously varying the sound intensity of selected emitters to create the perception of a relatively stationary sound horizon.

9 Claims, 7 Drawing Sheets

APPARATUS AND METHOD FOR REDUCING MOTION SICKNESS

BACKGROUND OF THE INVENTION

1. Field of the Invention

This invention relates to a sense of physical well-being in an individual and more particularly to the avoidance or reduction of motion sickness which many individuals experience when travelling on the water or in the air, as well as in space.

The invention is further related to the provision of an artificial sensory environment, through acoustic means, which may enable individuals to avoid or reduce the effects of motion sickness.

2. Description of the Related Art

It is generally recognized that motion sickness is greater in sailors working below deck than those above who have the horizon as a visual reference. This has led to the suggestion of the creation of an artificial visual horizon on board ship. See "Performance and Well-Being Under Tilting Conditions: The Effects of Visual Reference and Artificial Horizon" by A. Rolnick, Ph.D. and W. Bles, Ph.D., in *Aviation, Space and Environmental Medicine*, Aug. 1989, pages 779–785.

The attenuation of noise by sophisticated muff-type headsets in order to protect the hearing of a pilot is well recognized as for example in "The Art of Noise" in *AOPA PILOT*, pages 65–69, Dec. 1989. See also, "Fighting Noise With Antinoise", TIME, Dec. 4, 1989, page 94.

The Kuehn U.S. Pat. No. 4,283,798 discloses a diver's helmet which has a series of mercury switches that are responsive to the tilting of the diver's head about the various axes and which operate light emitting diodes that are spaced around the periphery of the face plate in order to indicate visually the true horizon.

The Clancy U.S. Pat. No. 2,288,683 discloses an automobile which has sensing means that are responsive to inclination of the vehicle and other movements and which operate a sound medium within the vehicle.

The Trumble U.S. Pat. No. 3,461,423 discloses a tone generator which is responsive to acceleration or impact of the vehicle The McGregor et al. U.S. Pat. No. 4,052,720 discloses the use of speakers in a room which are responsive to various environmental sound detectors and which adjust and shape the output from the speakers in response to such factors as background noise level The Warnaka et al. U.S. Pat. No. 4,562,589 discloses the use of a noise sensor within an airplane which is adapted to produce noise out of phase with the source noise in order to cancel out some of the source noise.

The Fedor U.S. Pat. No. 1,907,402, Leffler U.S. Pat. No. 2,745,091, Boyd et al. U.S. Pat. No. 3,548,400, and Gibson et al. U.S. Pat. No. 4,284,987 disclose means for sensing the inclination or tilt of a vehicle or the like and operating a signal in response thereto.

The article published by Dr. Gillingham in USAF-SAM/VN/AV240-3521 discloses an Acoustic Orientation Instrument which has been installed in a T-40 flight simulator as an approach to situational awareness. According to the article the instrument represents air speed as sound frequency, vertical velocity as amplitude modulation rate, angle of attack as an overlaid stutter signal, and bank as the amount of right or left lateralization of the sound signal.

SUMMARY OF THE INVENTION

The invention includes a method and apparatus for sensing the angular and vertical accelerations of an enclosure and providing an artificial inertially stable horizon of sound within the enclosure as a reference, by positioning sound emitters on or at the sides of the enclosure and varying the sound levels from selected emitters in response to changes in the enclosure's movement, to maintain the stable horizon or reference position.

As indicated above, motion sickness appears to be worse in sailors who are stationed below deck than those above deck who have a view of the horizon. The explanation appears to be that motion sickness occurs when there is an unaccustomed mismatch between the various perceived sources of spatial information. For example, the vestibular system senses motion due to tilting or to inertial movements, but to a passenger in a confined cabin his visual perception is stationary. Hence there is a conflict between the passenger's vestibular and visual senses. However if the passenger can see the horizon, then his vestibular and visual perceptions are in accord and the likelihood of motion sickness is diminished.

Motion information is received by an individual not only through the vestibular and visual senses but also through the acoustic sense. Thus, the apparent matching or mismatching of the vestibular senses with the acoustic may have an effect on the motion sickness or well-being of an individual. To a stationary occupant in an enclosed irregularly moving vehicle, whose sounds primarily emanate from within the vehicle, both sight and hearing provide information that the vehicle is stationary while the inertial inputs of the vestibular senses give information that the vehicle is in irregular motion. In accordance with the present invention, the vestibular-sensory conflict which may lead to motion sickness in angularly accelerated and vertically accelerated vehicles is reduced by the production of sounds which are stereophonically coordinated with the vehicle's movement so that the sounds are perceived to be stationary relative to the horizon or to a point on the horizon. This apparent source of sound that does not accelerate relative to the earth (in distinction to an ordinary sound-source fixed within an irregularly moving vehicle) constitutes an auditory input that is in accordance with the sense of motion provided by the occupant's vestibular system and thereby reduces the vestibular-sensory conflict that provokes motion sickness.

Thus, the present invention includes a means and procedure for providing acoustic information that matches that received from the vestibular senses. This is done by creating an apparent source of sound that is substantially fixed upon the horizon. Just as an object viewed upon the horizon gives visual information in accordance with prevailing inertial inputs, so too, the acoustic object which is stable on the horizon reduces the sensory conflict.

DESCRIPTION OF A PREFERRED EMBODIMENT

Figure 1:
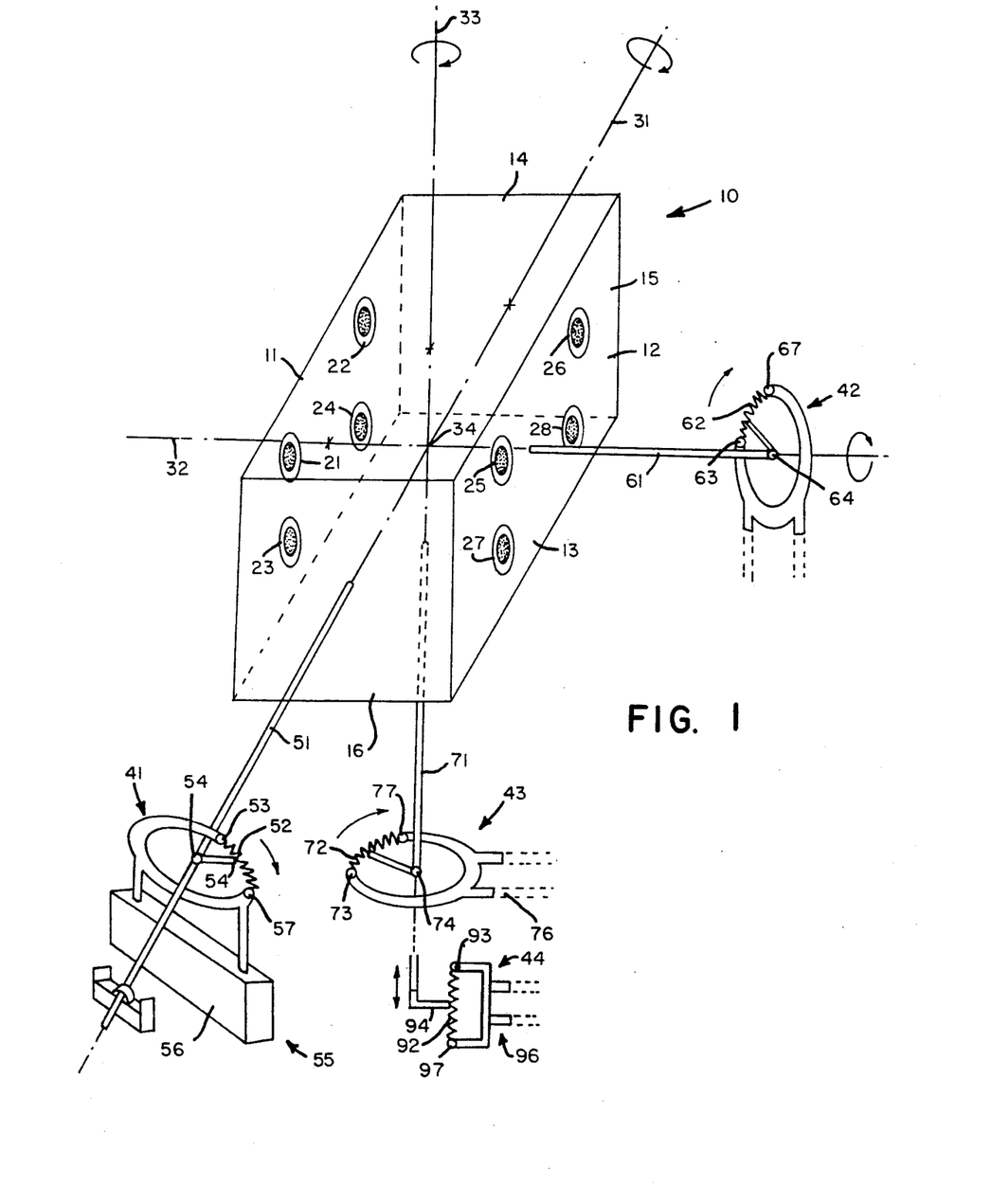
FIG. 1 is a schematic illustration of an enclosure with a sound system therein in accordance with the present invention; and, FIG. 2 is a diagrammatic illustration of a vertical section through a boat hull in different roll positions and indicating the stable horizon of sound in accordance with the present invention.

With further reference to the drawings an enclosure 10 is illustrated which has a left or port wall 11, a right or starboard wall 12, a lower and upper wall 13 and 14 and a forward and rear wall 15 and 16. A left wall 11 is provided with upper rearwardly and forwardly positioned speakers 21 and 22 and lower rearwardly and forwardly positioned speakers 23 and 24. Similarly the right wall 12 is provided with upper rearwardly and forwardly positioned speakers 25 and 26 and lower rearwardly and forwardly positioned speakers 27 and 28.

The enclosure is seen as having a longitudinal axis 31, a lateral axis 32 and a vertical axis 33 which axis intersect at a center of gravity 34. An attitude sensor 41 is provided for the axis 31, a sensor 42 is provided for the axis 32 and sensors 43 and 44 are provided for the axis 33.

In the illustrated embodiment each of the attitude sensors includes a rheostat with its shaft connected to the vehicle along the axis indicated so that the rheostat shaft moves with the vehicle as it turns about the axis or moves along the axis. The rheostat housing is stabilized relative to movements of the shaft, by angular or linear inertia increasing means well known in the art such as a gyroscope or a spring damped pendulum.

Thus, the attitude sensor 41 has a rheostat shaft 51, a resistance element 52, terminal points 53 and 57, moving contact 54, common to all of the speaker volume controls, with contact point 54', and means 55 for stabilizing of the housing of the rheostat on which the electrical resistance element 52 is mounted. In the drawing there is illustrated a spring damped pendulum 56 which is fastened to the rheostat housing.

Similarly, on the lateral axis 32 attitude sensor 42 includes a rheostat shaft 61, an electrical resistance 62, terminal points 63 and 67, and contact 64 in common with control 54. Rheostat 62 may be stabilized in the same manner as rheostat 52.

With reference to the vertical axis 33 and attitude sensor 43, rheostat shaft 71 has a resistance 72 with terminal points 73 and 77, and contact 74 in common with contacts 54 and 64. The housing for rheostat 73 may be stabilized by being connected to a gyroscope, not shown, through leads 76.

With further reference to vertical axis 33 and the vertical movement attitude sensor 44, rheostat shaft 71 has another resistance 92 with vertically spaced terminal points 93 and 97, and contact 94 in common with contacts 54, 64 and 74. The housing for resistance 92 may be stabilized by being connected to a spring-damped mass or gyroscope through leads 96.

The attitude sensors 41, 42, 43 and 44 are electrically connected to the speakers 21-28 in such a way that stereophonic shifts in the position of the sound's origin are in a direction to compensate for the roll, pitch, yaw or rise and fall of the vehicle so that the generated sound is perceived to be stable in the plane of the horizon (roll and pitch and rise and fall) or stable on a compass bearing (yaw). The combinations of speakers required for this varies with the axis around which the vehicle accelerates and whether the center of gravity of the vehicle accelerates on the vertical axis. In the illustrated embodiment, as previously stated, electrical contacts 54, 64, 74 and 94 are common to one side of the volume control circuits of all of the speakers. Terminal 53 is connected to the other side of the circuits of speakers 21, 22, 27 and 28. Terminal 57 is connected to the other side of the circuits of speakers 23, 24, 25 and 26.

The rheostats are connected electrically to control the volume of the speakers. For example, movement around axis 31 causes shaft 51 to move contact 54, along resistance 52. This changes the resistance between contact 54 and terminals 53 and 57, one increasing as the other decreases, proportionately If the movement is clockwise, looking toward the rear from the front, then electrical resistance between contact 54 and terminal 53 decreases, as resistance between contact 54 and terminal 57 increases. The resistance gradient should be steep enough to move the apparent source of sound in correspondence to the angular movement of the room.

Hence, in the illustrated embodiment a clockwise roll on the axis 31 increases the loudness of speakers 23, 24, 25 and 26 and decreases the loudness of speakers 21, 22, 27 and 28. This creates an apparent movement of the sound away from speakers 21, 22, 27 and 28 towards speakers 23, 24, 25 and 26 in proportion to the clockwise roll of the vehicle and in so doing stabilizes a sound source on the horizon that has a directional component along the vehicle's lateral axis.

Stated differently, the sound source is not perceived as rolling with the vehicle but rather is inertially stable while the vehicle rolls relative to the sound source such as a sound source on a nearby dock. Under these conditions the acoustic perceptions in reference to the stabilized sound source are in accordance with the vestibular input while any acoustic perceptions in reference to the unstabilized sources, that is, within the boat itself, are in conflict with the vestibular input.

Figure 2:
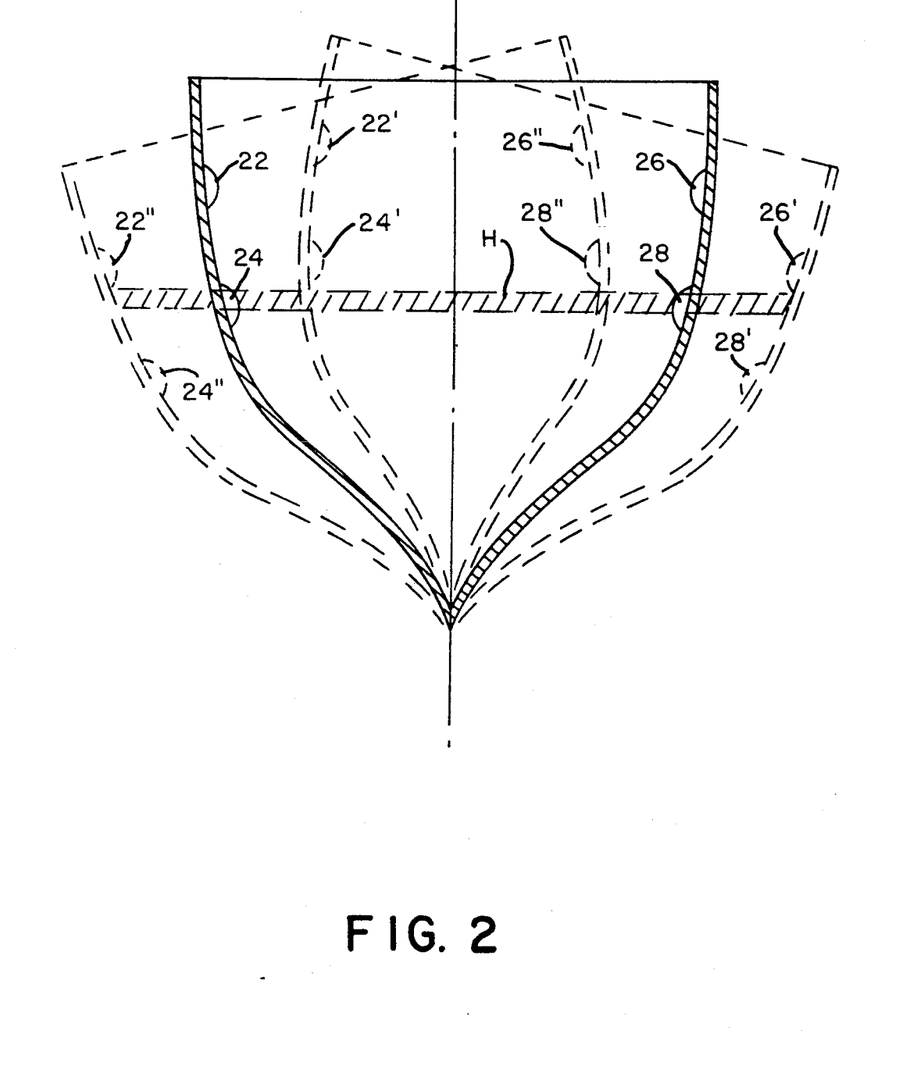
Figure 3A:
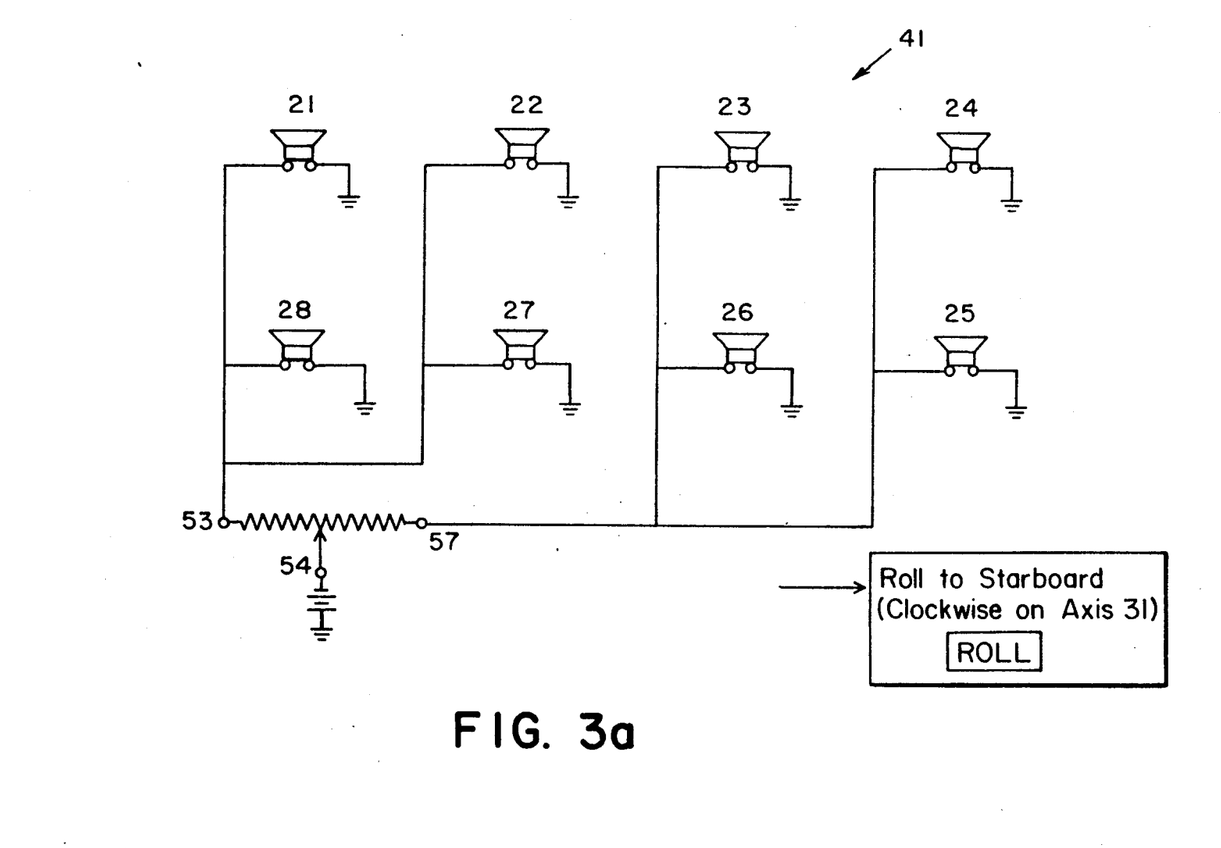
FIG. 3a-3d is a proposed schematic circuit.
Figure 3B:
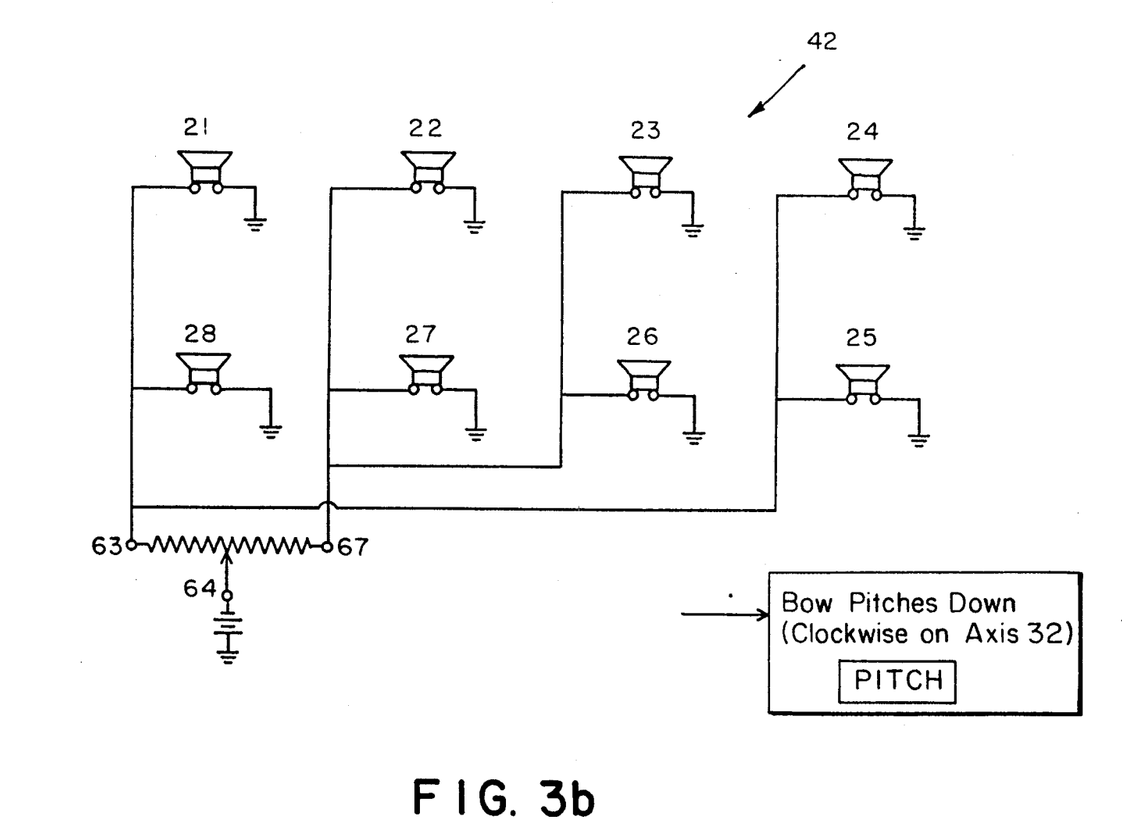
Figure 3C:
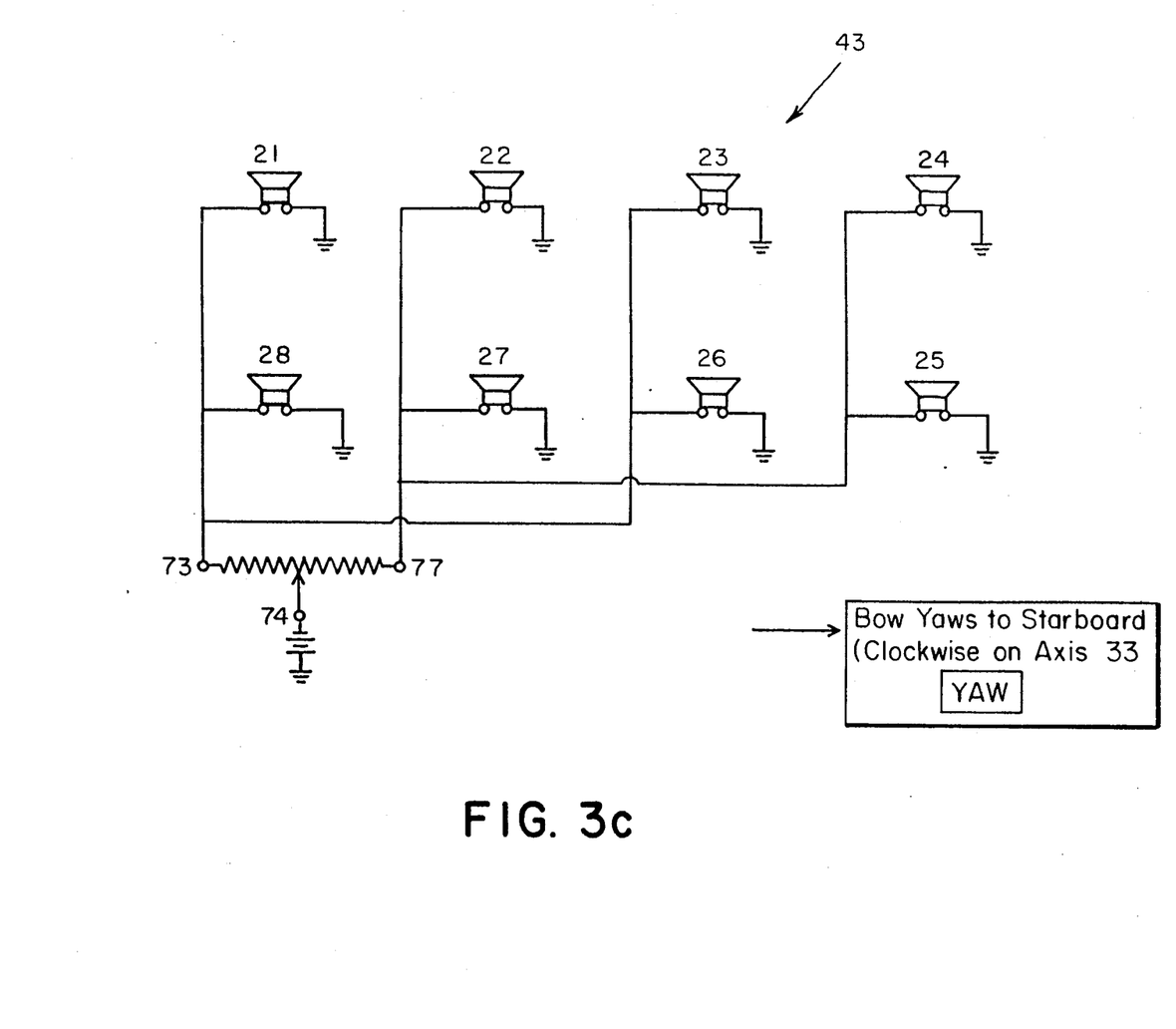
Figure 3D:
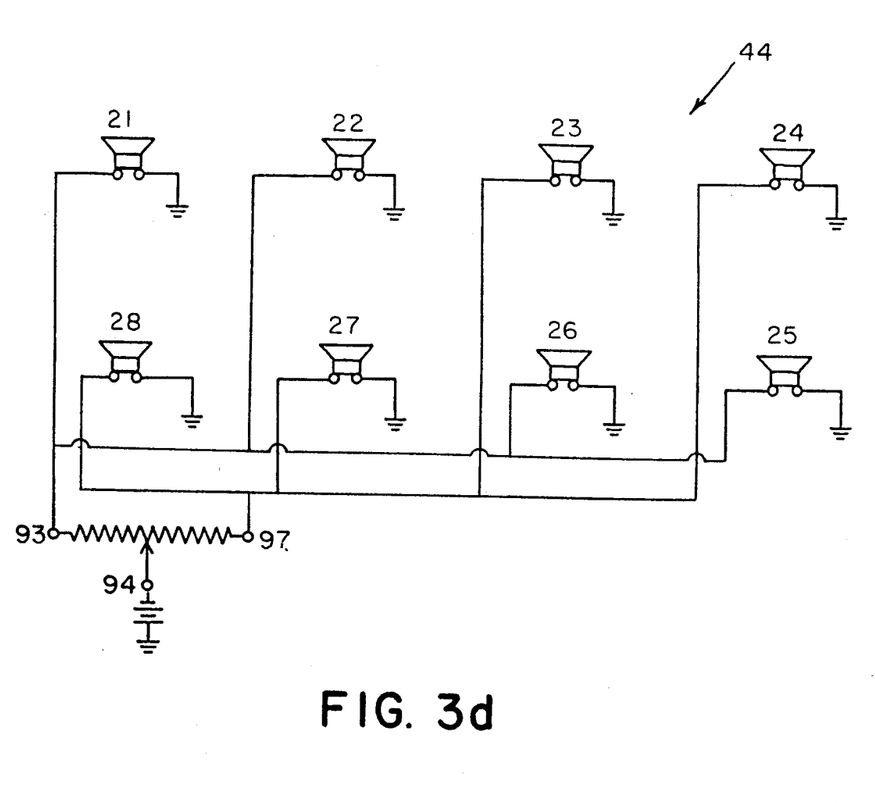

FIG. 2 illustrates how the positions of the various speakers change as the boat rolls about the axis 31. Thus, with reference to FIG. 2 it will be perceived that as the vessel rolls to the right, as viewed in FIG. 2, that a horizon of sound H will be produced between the speaker in the position 24' and the opposite speaker in the position 26'which horizon of sound will be substantially the same as that perceived prior to rolling of the vessel.

Similarly, upon the rolling of the boat about the axis 31 to the other extreme, the volume will be increased through the speaker in the position 28" and the speaker in the position 22", which thereby maintains the horizon of sound substantially as had existed theretofore.

As the boat returns to the central position the volume of sound likewise is changed so that in the central position in which the sound level is the same through all of the speakers the horizon of sound will coincide substantially with that which was achieved at the two extremes of the roll about the axis 31.

With reference to the attitude sensor 42, contacts 54, 64, 74 and 94 are common to all speakers, as previously described. Terminal 63 is connected to the other side of speakers 21, 25, 24 and 28. Terminal 67 is connected to speakers 23, 27, 22 and 26. Hence, a clockwise pitch on the axis 32, as viewed in FIG. 1., increases the loudness of speakers 23, 27, 22 and 26 and decreases the loudness of speakers 21, 25, 24, and 28. This creates an apparent movement of the sound away from the speakers 21 and 25 and towards the speakers 23 and 27 in proportion to the clockwise pitch of the vehicle and therefore stabilizes the sound source on the horizon and has a directional component along the vehicle's longitudinal axis.

Referring to attitude sensor 43, contacts 54, 64, 74 and 94 are common to all speakers, as described. Terminal 73 is connected to the other side of speakers 26, 28, 21 and 23. Terminal 77 is connected to speakers 22, 24, 25 and 27. A clockwise yaw on the axis 71 increases the loudness of speakers 22, 24, 25 and 27 and decreases the loudness of speakers 26, 28, 21 and 23. This creates an apparent movement of the sound away from speakers 26 and 28 and towards speakers 22 and 24 in proportion to the clockwise yaw of the vehicle and thus stabilizes a sound source at a given compass heading. This sound source does not change direction with the yaw of the vehicle and thus furnishes acoustic input that supports information from the vestibular sense thereby reducing the vestibular-sensory conflict known to lead to motion sickness.

On axis 32, terminal 63 is connected from contact 64 to volume control circuits of speakers 21, 28, 24 and 25. Terminal 67 is connected to volume control circuits of speakers 22, 27, 23 and 26.

On axis 33, terminal 73 is connected from contact 74 to volume control circuits of speakers 21, 28, 23 and 26. Terminal 77 is connected to volume control circuits of speakers 22, 27, 24 and 25.

Referring to attitude sensor 44, contacts 54, 64, 74 and 94 are common to all speakers, as described. Terminal 93 is connected to the other side of speakers 21, 22, 25 and 26. Terminal 97 is connected to speakers 23, 24, 27 and 28. A vertical drop on axis 71 increases the loudness of speakers 21, 22, 25 and 26 and decreases the loudness of speakers 23, 24, 27 and 28. This creates an apparent movement of the sound away from speakers 23, 24, 27 and 28 and towards speakers 21, 22, 25 and 26 in proportion to the vertical drop of the vehicle and thus stabilizes a sound source on the horizon.

The rheostats connecting the terminals described above are connected to the speakers in such a way that a summation of the input electrical characteristic is provided for each speaker, thus varying its volume in accordance with the sum of the inputs from the three axes 31, 32 and 33. This may be accomplished by the use of individual circuits as indicated in FIG. 3a, 3b, 3c and 3d.

Figure 4:
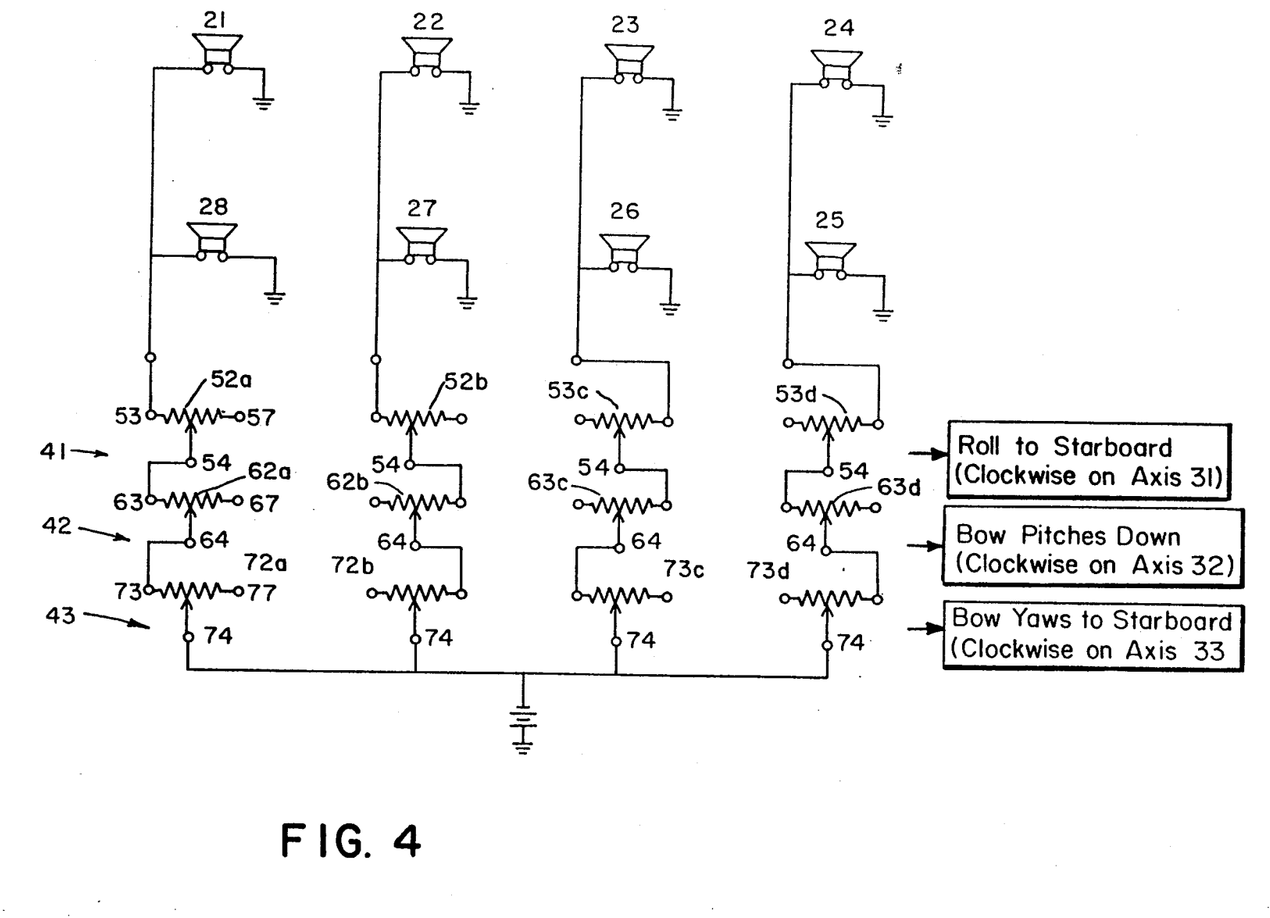
FIG. 4 is an alternative schematic circuit diagram.

Alternatively, a circuit like FIG. 4 may be used. In FIG. 4, the three rheostats, measuring acceleration around the three axes, which may affect each pair of speakers are connected in series. Each attitude sensor 41, 42 and 43 is constructed and arranged to control the circuit to four pairs of speakers. The attitude sensors may be separate or segmented.

Thus, in FIG. 4, rheostats 52a, 62a and 72a are connected between the power source and speakers 21 and 28, the rheostats being controlled by sensors 41, 42 and 43, respectively. Similarly, rheostats 52b, 62b and 72b connect the power source and speakers 22 and 27. Rheostats 53c, 62c and 72c connect the power source and speakers 23 and 26. And, rheostats 53d, 62d and 72d connect the power source and speakers 24 and 25. In the foregoing, sensor 41 controls rheostats 52a-52d; sensor 42 controls rheostats 62a-62d; and sensor 43 controls rheostats 72a-72d.

While rheostats have been illustrated as a method of dividing or controlling the volume or loudness output, by for example, controlling the current to the speakers, other means well known in the art such as magnetic coils which work on the principle of magnetic induction may also be used. This might include for example an accelerometer feeding into a microprocessor.

While different kinds of sound emitters may be employed, in the practice of the present invention it is believed that sound sources that are easily perceived over the background noise and which are indicative or perceived to be indicative of a direction are preferred. Further, the use of the system of the present invention may require attenuation of the background noise. A typical use of the invention would be in a cabin in a boat or a cruise ship employing an automatic stereo system, or the system may be employed in an aircraft cabin or in the housing of a space capsule. It is also apparent that even though a series of four speakers mounted in parallel walls has been described that varying numbers and arrangements of speakers may be employed to accomplish a useful result.

This arrangement of speakers may include their reduction in size and the reduction of the distance of their separation so that they function as earphones. The angular and vertical acceleration sensors would be mounted so they would move with the head of the user and may include these sensor's being made sufficiently small to be incorporated within the earphones. In this embodiment of the invention the size of the enclosure 10 is reduced to the interaural distance of the user. This allows the maintenance of a stable acoustic horizon during combined movements of the vehicle and self-produced movements of the head of the user Although selective variations in the sound volume from the positioned speakers has been described as the means for providing a perceived substantially stationary horizon o sound, the invention also contemplates that apparent sound position variations may be accomplished by various stereophonic means, including varying the phase of the sound Phase variation as a cue for sound localization is described, for example, in Directional hearing in terrestrial mammals. In Comparative Studies of Hearing in Vertebrates. Popper, A.N. Fay, R.R. (eds.), New York: Springer-Verlag, 1980, pp357-373. Phase variation to reduce noise in a cockpit is described, for example in "The Art of Noise", by Marc E. Cook, *AOPA Pilot*, Dec. 1989, pp 66–69, and in *Time*, Dec. 4, 1989, page 94.

I claim:

1. The method of reducing the effect of motion induced sickness in an individual subjected to irregular angular and irregular vertical motion in a compartment which is moving with reference to a fixed horizon which horizon is independent of the compartment's orientation, comprising creating an artificial sound horizon which is acoustically perceivable to the individual and continuously maintaining such sound horizon substantially positionally stationary with reference to the fixed horizon.

2. Apparatus for relieving the onset or severity of motion sickness which is caused by the angular and heaving motion of an enclosure or compartment of a ship in the water, a plane in the air, or a spacecraft in space, comprising mounting two or more sound emitters on a side of the enclosure, at least two of said emitters being mounted at different elevations in the enclosure, means for sensing the angular movement of the enclosure away from a predetermined reference position, and varying the volume of sound selectively from the emitters as the enclosure moves away from the reference position, thereby creating a continuously perceivable inertially stable, substantially stationary sound horizon in the enclosure.

3. The invention of claim 2 in which the enclosure has side means lying in substantially parallel planes, and a plurality of sound emitters in said side means, each side means having at least a first and a second emitter, said first emitter being mounted at a different elevation than said second emitter.

4. The invention of claim 3, in which said second emitter is mounted forwardly of said second emitter.

5. The invention of claim 3 in which the enclosure has left and right side means lying in planes substantially parallel to the longitudinal axis of the ship, plane or spacecraft.

6. The invention of claim 2 in which the enclosure has first and second side means lying in spaced substantially parallel planes and at least four emitters in said side means, said first side means having a first and second emitter positioned at an upper level in said enclosure, third and fourth emitters positioned at a lower level, said first and third emitters positioned rearwardly of said second and fourth emitters, said second side means having a fifth and sixth emitter positioned at an upper level in said enclosure and a seventh and eighth emitter positioned at a lower level in said enclosure, said fifth and seventh emitters positioned rearwardly of said sixth and eighth emitters.

7. The invention of claim 5 in which the enclosure has left and right side means substantially parallel to the longitudinal axis of the ship.

8. The invention of claim 2 in which the means for creating an apparent source of sound that is substantially fixed upon the horizon varies the loudness level.

9. The invention of claim 2 in which the means for creating an apparent source of sound that is substantially fixed upon the horizon varies the phase of the sound.

* * * * *